United States Patent [19]

Aizono et al.

[11] Patent Number: 5,808,169
[45] Date of Patent: Sep. 15, 1998

[54] PROCESS FOR THE PREPARATION OF 1,2,4,5-DIMETHYLDIISOPROPYLBENZENE

[75] Inventors: Hirofumi Aizono; Takeshi Kouchi; Kazuto Hironaga, all of Kanagawa, Japan

[73] Assignee: Mitsubishi Oil Co., Ltd., Tokyo, Japan

[21] Appl. No.: 912,750

[22] Filed: Aug. 18, 1997

Related U.S. Application Data

[63] Continuation of Ser. No. 533,197, Sep. 25, 1995, abandoned.

[30] Foreign Application Priority Data

Sep. 27, 1994 [JP] Japan ................................ 6-256083

[51] Int. Cl.$^6$ ................................ C07C 2/70; C07C 7/14
[52] U.S. Cl. ........................ 585/446; 585/323; 585/466; 585/804; 585/812
[58] Field of Search ............................ 585/323, 446, 585/804, 466, 812

[56] References Cited

U.S. PATENT DOCUMENTS 5,202,516  4/1993  Lee et al. ............................ 585/804
5,254,766  10/1993  Fujita et al. ......................... 585/446
5,488,194  1/1996  Beck et al. .......................... 585/446

OTHER PUBLICATIONS

Derwent Abstract–68:104964, "Preparation of 1,4–dimethyl–2,5–diisopropylbenzene", Babin et al, USSR, 1967.

*Primary Examiner*—Glenn Caldarola
*Assistant Examiner*—Thuan D. Dang
*Attorney, Agent, or Firm*—Sughrue, Mion, Zinn, Macpeak & Seas, PLLC

[57] ABSTRACT

A process for preparing 1,2,4,5-dimethyldiisopropylbenzene includes conducting alkylation of p-xylene with propylene to produce an alkylation product, and crystallizing the alkylation product. A heteropolyacid-supported catalyst can be used as an alkylation catalyst for the reaction. The reaction solution produced from the alkylation reaction can be distilled before crystallization to improve yield and purity even more.

4 Claims, No Drawings

PROCESS FOR THE PREPARATION OF 1,2,4,5-DIMETHYLDIISOPROPYLBENZENE

This is a Continuation of application Ser. No. 08/533,197 filed Sep. 25, 1995, now abandoned.

FIELD OF THE INVENTION

The present invention relates to a process for the preparation of 1,2,4,5-dimethyldiisopropylbenzene. More particularly, the present invention relates to a process for the preparation of a high purity 1,2,4,5-dimethyldiisopropylbenzene, which comprises the crystallization of the alkylation product of p-xylene with propylene to prepare 1,2,4,5-dimethyldiisopropylbenzene.

BACKGROUND OF THE INVENTION 1,2,4,5-Dimethyldialkylbenzene can be obtained by the alkylation of xylene with an olefin or alcohol. However, any method for the synthesis of 1,2,4,5-dimethyldialkylbenzene inevitably produces isomers such as 1,2,3,5-dimethyldialkylbenzene besides 1,2,4,5-dimethyldialkylbenzene as a starting material for making pyromellitic anhydride or the like. These isomers are alike in physical properties, and no methods have been known for efficiently isolating the desired 1,2,4,5-dimethyldialkylbenzene at a low cost. The presence of these isomers causes the following problems in the oxidation reaction step in the preparation of pyromellitic acid or pyromellitic anhydride:

(1) the presence of these isomers reduces the oxidation efficiency, reducing the yield of pyromellitic anhydride;

(2) the presence of these isomers also reduces the purity of the resulting pyromellitic anhydride; and (3) the presence of these isomers further reduces the life and activity of the catalyst for use in the oxidation reaction.

These problems are economically undesirable. Thus, the industry requires 1,2,4,5-dimethyldialkylbenzene having a purity as high as not less than 95% by weight.

SUMMARY OF THE INVENTION

An object of the present invention is to provide a process for the efficient preparation of a high purity 1,2,4,5-dimethyldiisopropylbenzene.

To satisfy this object, the inventors made extensive studies to solve the foregoing problems in the preparation of 1,2,4,5-dimethyldialkylbenzene. As a result, it was found that the combination of synthesis using specific materials and crystallization can provide easy preparation of a high purity 1,2,4,5-dimethyldialkylbenzene. In greater detail, it has been found that the crystallization of the specific reaction product of p-xylene and propylene as starting materials in an alkylation reaction can provide easy preparation of a high purity 1,2,4,5-dimethyldiisopropylbenzene as a starting material for making pyromellitic anhydride, etc. Thus, the present invention has been worked out.

DETAILED DESCRIPTION OF THE INVENTION 1,2,4,5-Dimethyldialkylbenzene can be obtained by the alkylation of o-xylene, m-xylene, p-xylene or a mixture thereof as a starting material with methanol or an olefin. In the present invention, 1,2,4,5-dimethyldiisopropylbenzene is prepared from p-xylene and propylene in particular as starting materials. Strictly speaking, 1,2,4,5-dimethyldiisopropylbenzene is called 1,4-di-methyl-2,5-diisopropylbenzene in the light of the position of the alkyl group on the benzene ring. However, it is hereinafter referred to as "1,2,4,5-dimethyldiisopropylbenzene" for convenience. It is difficult to crystallize and purify 1,2,4,5-dimethyldialkylbenzene synthesized from o-xylene, m-xylene or a xylene mixture as a starting material.

Examples of the alkylating agent for p-xylene include methanol and olefins. If methanol is used as the alkylating agent for p-xylene, the resulting product is durene. Durene is most suitable as a starting material of pyromellitic acid. However, the said method generally produces a large amount of 1,2,3,5-dimethyldiisopropylbenzene as a by-product. Thus, the crystallization of the reaction product cannot be efficiently effected. If a zeolite catalyst having a shape selectivity is used, the selectivity of 1,2,4,5-dimethyldiisopropylbenzene can be enhanced. However, the use of such a catalyst generally gives a reduced yield, for example, 30–40 wt. % on starting material. Examples of olefins include ethylene, propylene, 1-butene, cis 2-butene, trans 2-butene, 1-pentene, and isopentene. All these olefins can help produce 1,2,4,5-dimethyldialkylbenzene at a high selectivity. However, the use of these olefins gives a reduced yield, i.e., less than 60 wt. %, except propylene. In the present invention, propylene is used.

The alkylation reaction of p-xylene for the preparation of 1,2,4,5-dimethyldiisopropylbenzene can be accomplished by a catalytic reaction. Examples of the catalyst which can be employed in the catalytic reaction include solid acid catalysts such as silica alumina and zeolites (JP-A-48-85540 (the term "JP-A" as used herein means an "unexamined Japanese Patent Publication")), cation exchange resins (JP-A-48-19526), and heteropolyacid and/or heteropolyacid salt-supported catalysts (JP-A-05-9135).

Any of these methods can be used to provide the desired 1,2,4,5-dimethyldiisopropylbenzene. A solid acid catalyst such as silica alumina or a zeolite can provide a satisfactory yield (around 90 wt. %) of dimethyldiisopropylbenzene. However, such a solid acid catalyst is disadvantageous in that it has a short life. Thus, such a solid acid catalyst cannot be easily put into practical use. The cation exchange resins have a low thermal stability and thus are generally impractical. As mentioned above, a heteropolyacid and/or heteropolyacid salt-supported catalyst is preferably used from the standpoint of the practicality of the catalyst. Thus, a heteropolyacid-supported catalyst can be used as an alkylation catalyst. In such an embodiment, the present invention is directed to a process for the preparation of 1,2,4,5-dimethyldiisopropylbenzene, which comprises the crystallization of the alkylation product of p-xylene with propylene in the presence of a heteropolyacid-supported catalyst to prepare 1,2,4,5-dimethyldiisopropylbenzene, desirably with a purity of not less than 95%.

The foregoing heteropolyacid and/or heteropolyacid salt-supported catalyst may comprise any heteropolyacid or heteropolyacid salt without hindrance. Specific examples of such a heteropolyacid or heteropolyacid salt include dodecaphosphotungstic acid ($H_3PW_{12}O_{40}$), dodecasilicotungstic acid ($H_4SiW_{12}O_{40}$), dodecaphosphomolybdic acid ($H_3PMo_{12}O_{40}$), dodecagermatungstic acid ($H_3GeW_{12}O_{40}$), and dodecagermamolybdic acid ($H_3GeMo_{12}O_{40}$). Examples of the heteropolyacid salt employable herein include compounds obtained by partially or entirely substituting hydrogen atoms in the foregoing heteropolyacids by alkaline metals, alkaline earth metals, various transition metals or amines. As the carrier, there may be used silica gel, titania, activated carbon or the like. An impregnation method may be used to prepare the foregoing heteropolyacid and/or heteropolyacid salt-supported catalyst. The supported amount of heteropolyacid can be from 1 to 50% by weight, preferably from 10 to 40% by weight based on the total weight of the catalyst.

In the alkylation reaction of p-xylene with propylene, either a continuous or batchwise reaction vessel can be used. Referring to the reaction conditions, the molar ratio of propylene/p-xylene can be from 1.0 to 5.0, preferably from 2.0 to 4.0, the reaction temperature can be from 70° C. to 200° C., preferably from 100° C. to 150° C., and the reaction pressure can be from normal pressure to 10 kg/cm$^2$, preferably from 2 to 8 kg/cm$^2$. In the case where a continuous reaction vessel is employed, the starting materials may be supplied into the reaction zone at a weight unit hour space velocity (WHSV) of from 0.1 to 10 hr$^{-1}$, preferably from 0.5 to 6.0 hr$^{-1}$.

The main reaction product is dimethyldiisopropylbenzene. The reaction solution contains unreacted starting materials, and by-products such as dimethylisopropylbenzene and dimethyltriisopropylbenzene. The dimethyldiisopropylbenzene contains isomers in addition to 1,2,4,5-dimethyldiisopropylbenzene. Whatever the composition is, the reaction solution can be crystallized and purified to prepare 1,2,4,5-dimethyldiisopropylbenzene. However, the concentration of 1,2,4,5-dimethyldiisopropylbenzene in the reaction product is preferably not less than 60% by weight from the standpoint of efficiency in an industrially practical operation. If necessary, this reaction product can be subjected to any ordinary process to separate the catalyst and other undesirable components therefrom, followed by crystallization. This is because the combination of p-xylene and propylene enables a high yield and selectivity production of 1,2,4,5-dimethyldiisopropylbenzene. However, it is more effective to distill the reaction solution before crystallization from the standpoint of yield and purity. The distillation may be effected under any conditions as long as dimethyldiisopropylbenzene can be separated from the other fractions. If effected at normal pressure, the distillation temperature can be from 150° C. to 300° C., preferably from 170° C. to 250° C.

In the present invention, the reaction product is purified by crystallization. The crystallization may be accomplished by any method which comprises the production of crystalline substances. Examples of such a crystallization method include cooling crystallization and pressure crystallization. However, cooling crystallization is preferred from the standpoint of the yield of 1,2,4,5-dimethyldiisopropylbenzene and the economy and simplicity of the apparatus.

In the cooling crystallization process, the cooling temperature may be not higher than the temperature at which 1,2,4,5-dimethyldiisopropylbenzene crystallizes out, although it can depend on the concentration of 1,2,4,5-dimethyldiisopropylbenzene in the reaction product of p-xylene and propylene as starting materials. The cooling temperature is normally not higher than 10° C., preferably from −15° C. to 5° C. The higher the cooling temperature is, the higher the purity of the resulting 1,2,4,5-dimethyldiisopropylbenzene is, but the lower its yield is. Thus, the optimum cooling temperature may be selected depending on the required concentration of 1,2,4,5-dimethyldiisopropylbenzene in the reaction product. If the purity of the product needs to be further increased, any processing such as recrystallization may be additionally effected. In the pressure crystallization process, the crystallization pressure can be from 1,000 kgf/cm$^2$ to 5,000 kgf/cm$^2$.

The product which has thus been crystallized by cooling crystallization or pressure crystallization is then subjected to a suitable process such as press filtration or centrifugal filtration to effect solid-liquid separation so that the crystal is withdrawn as the purified product. The crystallization temperature is preferably continued in this process to prevent the loss of 1,2,4,5-dimethyldiisopropylbenzene by dissolution in the liquid phase. If cooling crystallization and press filtration are used in combination, the product of alkylation of p-xylene with propylene or its distillate is charged into a cooling vessel. The material is then cooled to a predetermined temperature in a constant temperature bath. Once the material crystallizes out, the slurry is then moved into a piston vessel equipped with a filter for pressing. The slurry is then pressed to separate the crystal from the filtrate. In this manner, a crystal mainly composed of 1,2,4,5-dimethyldiisopropylbenzene can be obtained. The higher the pressure applied to the piston vessel is, the shorter the time is during which solid-liquid separation can be effected. The pressure is determined by the required purity of 1,2,4,5-dimethyldiisopropylbenzene.

The purity of the 1,2,4,5-dimethyldiisopropylbenzene produced according to the present invention is preferably at least 90%, more preferably at least 95%.

The present invention will be further described in the following examples, but the present invention should not be construed as being limited thereto. Unless otherwise indicated, all parts, percents, ratios and the like are by weight.

EXAMPLE

Propylene and p-xylene were supplied as starting materials into the reaction zone of a fixed bed catalytic reaction vessel in a propylene/p-xylene molar ratio of 3.5 where they were allowed to undergo reaction in the presence of a silica gel having 20% by weight of dodecasilicotungstic acid supported thereon as a heteropolyacid-supported catalyst at a reaction pressure of 4.5 kgf/cm$^2$, a reaction temperature of 107° C. and a WHSV of 2.0 hr$^{-1}$. The resulting reaction product was subjected to quantitative analysis by gas chromatography. As a result, a mixture of 67.2 mol % of 1,2,4,5-dimethyldiisopropylbenzene, 18.7 mol % of 1,2,3,5-dimethyldiisopropylbenzene, 1.3 mol % of p-xylene, 10.7 mol % of dimethylisopropylbenzene, and 2.0 mol % of heavy fractions and other components was obtained. The mixture was subjected to cooling crystallization at a temperature of from −15° C. to 5° C., and then press-filtered at a pressure of 100 kgf/cm$^2$ for 0.5 hours. The purity of the resulting 1,2,4,5-dimethyldiisopropylbenzene and the yield of 1,2,4,5-dimethyldiisopropylbenzene in the reaction product are set forth in Table 1.

TABLE 1

| Cooling temperature (°C.) | −15 | −10 | −5 | 0 | 5 |
|---|---|---|---|---|---|
| % Purity of 1,2,4,5-DMDiPB | 92.1 | 93.8 | 94.5 | 94.9 | 95.2 |
| % Yield of 1,2,4,5-DMDiPB | 70.3 | 69.3 | 64.0 | 56.4 | 42.8 |

Note: DMDiPB stands for dimethyldiisopropylbenzene.

EXAMPLE 2

The product obtained by the reaction of Example 1 was distilled at normal pressure and distillation temperature, i.e., 170° to 250° C. by means of an apparatus having 30 theoretical plates. The resulting distillate was then subjected to quantitative analysis by gas chromatography. As a result, a mixture of 79.1 mol % of 1,2,4,5-dimethyldiisopropylbenzene, 19.6 mol % of 1,2,3,5-dimethyldiisopropylbenzene, and 1.3 mol % of dimethylisopropylbenzene and other components was obtained. The mixture was then crystallized and purified in the same manner as in Example 1. The purity of the resulting 1,2,4,5-dimethyldiisopropylbenzene and the yield of 1,2,4,5-dimethyldiisopropylbenzene in the reaction product are set forth in Table 2.

TABLE 2

| Cooling temperature (°C.) | −15 | −10 | −5 | 0 | 5 |
|---|---|---|---|---|---|
| % Purity of 1,2,4,5-DMDiPB | 94.4 | 95.3 | 96.1 | 96.4 | 97.2 |
| % Yield of 1,2,4,5-DMDiPB | 93.2 | 86.9 | 85.7 | 75.2 | 68.8 |

EXAMPLE 3

The product obtained by the reaction of Example 1 was processed in the same manner as in Example 1 except that pressure crystallization was effected at room temperature and 2,000 kgf/cm$^2$ instead of cooling crystallization. The resulting product was then subjected to quantitative analysis by gas chromatography. The purity of the resulting 1,2,4,5-dimethyldiisopropylbenzene was 98.3%. The yield of 1,2,4,5-dimethyldiisopropylbenzene on the reaction product was 34.3%.

COMPARATIVE EXAMPLE 1

A reaction was effected in the same manner as in Example 1 except that m-xylene was used instead of p-xylene. As a result, a mixture of 55.5 mol % of 1,2,4,5-dimethyldiisopropylbenzene and 24.7 mol % of 1,2,3,5-dimethyldiisopropylbenzene along with other components was obtained. The mixture was then distilled. As a result, a distillate containing 72.6 mol % of 1,2,4,5-dimethyldiisopropylbenzene and 27.2 mol % of 1,2,3,5-dimethyldiisopropylbenzene along with other components was obtained. The distillate was then subjected to cooling crystallization at a temperature of from −30° C. to 5° C. As a result, no crystals were produced. Thus, the purification of 1,2,4,5-dimethyldiisopropylbenzene by press filtration as in Example 2 was impossible.

COMPARATIVE EXAMPLE 2

A reaction was effected in the same manner as in Example 1 except that o-xylene was used instead of p-xylene. As a result, a mixture of 65.1 mol % of 1,2,4,5-dimethyldiisopropylbenzene and 19.9 mol % of 1,2,3,5-dimethyldiisopropylbenzene along with other components was obtained. The mixture was then distilled. As a result, a distillate containing 72.9 mol % of 1,2,4,5-dimethyldiisopropylbenzene and 22.8 mol % of 1,2,3,5-dimethyldiisopropylbenzene along with other components was obtained. The distillate was then subjected to cooling crystallization at a temperature of from −30° C. to 5° C. As a result, no crystals were produced. Thus, the purification of 1,2,4,5-dimethyldiisopropylbenzene by press filtration as in Example 2 was impossible.

Thus, the crystallization of the reaction product of p-xylene and propylene in the preparation of 1,2,4,5-dimethyldiisopropylbenzene can easily provide a high purity 1,2,4,5-dimethyldiisopropylbenzene which is industrially very useful as an intermediate product from which pyromellitic acid or pyromellitic anhydride can be produced. In particular, 1,2,4,5-tetraalkylbenzenes such as 1,2,4,5-dimethyldiisopropylbenzene undergo oxidation to produce pyromellitic anhydride or the like (see JP-B-44-29446 (the term "JP-B" as used herein means an "examined Japanese patent publication") and JP-B-45-4978). Pyromellitic acid or its anhydride has found wide application as a starting material for making a plasticizer or heat-resistant high molecular compound or epoxy resin hardener. It has thus been keenly desired to provide an economical supply of a high purity 1,2,4,5-dimethyldiisopropylbenzene as a starting material for making pyromellitic acid or its anhydride. The present invention satisfies this desire by providing an efficient process for the preparation of a high purity 1,2,4,5-dimethyldiisopropylbenzene.

While the invention has been described in detail and with reference to specific examples thereof, it will be apparent to one skilled in the art that various changes and modifications can be made therein without departing from the spirit and scope thereof.

What is claimed is:

1. A process for preparing 1,2,4,5-dimethyldiisopropylbenzene, which comprises conducting alkylation of p-xylene with propylene to produce an alkylation product, and purifying the alkylation product by crystallization to prepare 1,2,4,5-dimethyldiisopropylbenzene;

wherein a heteropolyacid-supported catalyst is used as an alkylation catalyst; and wherein the alkylation of p-xylene with propylene provides a reaction solution, which is directly purified by crystallization.

2. The process for preparing 1,2,4,5-dimethyldiisopropylbenzene according to claim 1, wherein the process consists essentially of conducting alkylation of p-xylene with propylene to produce an alkylation product, and purifying the alkylation product by crystallization to prepare 1,2,4,5-dimethyldiisopropylbenzene.

3. A process for preparing 1,2,4,5-dimethyldiisopropylbenzene while maintaining catalyst life, which comprises conducting alkylation of p-xylene with propylene to produce an alkylation product, and purifying the alkylation product by crystallization to prepare 1,2,4,5-dimethyldiisopropylbenzene;

wherein a heteropolyacid-supported catalyst is used as an alkylation catalyst in order to maintain catalyst life; and wherein the alkylation of p-xylene with propylene provides a reaction solution, which is directly purified by crystallization.

4. The process for preparing 1,2,4,5-dimethyldiisopropylbenzene according to claim 3, wherein the process consists essentially of conducting alkylation of p-xylene with propylene to produce an alkylation product, and purifying the alkylation product by crystallization to prepare 1,2,4,5-dimethyldiisopropylbenzene.

* * * * *